United States Patent
Bergin (10) Patent No.: US 8,398,707 B2
(45) Date of Patent: Mar. 19, 2013

(54) HEART VALVE HOLDER FOR USE IN VALVE IMPLANTATION PROCEDURES

(75) Inventor: Cathleen A. Bergin, Hugo, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 12/972,846

(22) Filed: Dec. 20, 2010

(65) Prior Publication Data

US 2011/0093064 A1 Apr. 21, 2011

Related U.S. Application Data (62) Division of application No. 11/888,696, filed on Aug. 2, 2007, now Pat. No. 7,871,432.

(60) Provisional application No. 60/835,366, filed on Aug. 2, 2006.

(51) Int. Cl.
  *A61F 2/24* (2006.01)
(52) U.S. Cl. ........................... 623/2.11; 606/108
(58) Field of Classification Search ................. 623/2.11, 623/1.11, 1.23; 606/108
  See application file for complete search history.

(56) References Cited

U.S. PATENT DOCUMENTS

| | | | |
|---|---|---|---|
| 4,106,129 A | 8/1978 | Carpentier et al. | |
| 4,865,600 A | 9/1989 | Carpentier et al. | |
| 4,990,151 A * | 2/1991 | Wallsten | 606/108 |
| 5,037,434 A | 8/1991 | Lane | |
| 5,476,510 A | 12/1995 | Eberhardt et al. | |
| 5,716,401 A | 2/1998 | Eberhardt et al. | |
| 5,800,531 A | 9/1998 | Cosgrove et al. | |
| 5,855,602 A | 1/1999 | Angell | |
| 5,861,028 A | 1/1999 | Angell | |
| 5,885,228 A | 3/1999 | Rosenman et al. | |
| 6,042,554 A | 3/2000 | Rosenman et al. | |
| 6,110,200 A | 8/2000 | Hinnenkamp | |
| 6,197,053 B1 | 3/2001 | Cosgrove et al. | |
| 6,702,852 B2 | 3/2004 | Stobie et al. | |
| 6,736,845 B2 | 5/2004 | Marquez et al. | |
| 6,893,459 B1 * | 5/2005 | Macoviak | 623/2.11 |
| 6,966,925 B2 | 11/2005 | Stobie | |
| 7,011,681 B2 * | 3/2006 | Vesely | 623/2.11 |
| 7,018,407 B1 | 3/2006 | Wright et al. | |
| 7,033,390 B2 | 4/2006 | Johnson et al. | |
| 7,189,258 B2 | 3/2007 | Johnson et al. | |
| 7,556,646 B2 * | 7/2009 | Yang et al. | 623/2.11 |
| 7,806,926 B2 * | 10/2010 | Stobie | 623/2.11 |
| 2004/0059412 A1 | 3/2004 | Lytle et al. | |
| 2005/0182486 A1 * | 8/2005 | Gabbay | 623/2.11 |
| 2006/0074486 A1 | 4/2006 | Liddicoat et al. | |
| 2006/0241743 A1 | 10/2006 | Bergin et al. | |
| 2007/0250160 A1 | 10/2007 | Rafiee | |

OTHER PUBLICATIONS

Medtronic Brochure, "A New Dimension—The Hancock II Bioprosthesis", Medtronic Inc., 1991, publication No. UC8903226EN, 8 pages.
Medtronic Brochure, "A New Light on the Hancock Bioprosthesis", Medtronic Inc., 1988, publication No. UC8801713EN, 13 pages.

\* cited by examiner

*Primary Examiner* — Julian Woo
*Assistant Examiner* — Christopher L Templeton (57) ABSTRACT

The invention features a valve holder for a prosthetic valve having a stent with a stent base and multiple commissure posts projecting from the stent base. The valve holder includes (i) a central base portion, (ii) a plurality of legs radially extending from the central base portion, and (iii) a handle extending from the central base portion. At least one of the legs of the holder has a first prong portion separated from a second prong portion by a gap. The leg also has a of commissure post engaging member that is slideably engaged with the leg.

4 Claims, 4 Drawing Sheets

HEART VALVE HOLDER FOR USE IN VALVE IMPLANTATION PROCEDURES

CROSS-REFERENCE TO RELATED APPLICATION

The present non-provisional patent application is a divisional of U.S. patent application Ser. No. 11/888,696, filed Aug. 2, 2007, now U.S. Pat. No. 7,871,432, which claims priority under 35 USC §119(e) from commonly owned provisional U.S. patent application Ser. No. 60/835,366, filed on Aug. 2, 2006, and titled "Heart Valve Holder For Use In Valve Implantation Procedures", the entire contents of which is incorporated herein by reference in its entirety.

TECHNICAL FIELD

The present invention relates generally to implantable valvular prostheses, and more particularly relates to a holding system or mechanism that can provide temporary prosthetic heart valve stent post deflection during implantation of valvular prostheses.

BACKGROUND OF THE INVENTION

Various types and configurations of prosthetic heart valves are used to replace diseased natural human heart valves. The actual shape and configuration of any particular prosthetic heart valve is dependent to some extent upon the valve being replaced (i.e., mitral valve, tricuspid valve, aortic valve, and pulmonary valve). In general terms, however, most prosthetic heart valve designs attempt to replicate the function of the valve being replaced and thus will include valve leaflet-like structures.

As used throughout this specification a "prosthetic heart valve having relatively flexible leaflets" or a "prosthetic heart valve" is intended to encompass bioprosthetic heart valves having leaflets made of a biological material as well as synthetic heart valves having leaflets made of a synthetic (e.g., polymeric) material. Either type of prosthetic heart valve can include a frame or stent or may have no such frame or stent. A stented prosthetic heart valve typically includes a stent having a substantially circular base (or stent ring), around which an annular suture material is disposed for suturing the prosthesis to heart tissue. The stent further typically includes at least two, but typically three, support structures extending from the stent ring. These support structures are commonly referred to as stent posts or commissure posts. These posts typically are rigid yet somewhat flexible structures extending from the stent ring, which are covered by a cloth-like material similar to that of the annular suture material or tissue. The stent or commissure posts define the juncture between adjacent tissue or synthetic leaflets otherwise secured thereto. Examples of bioprosthetic heart valves are described in U.S. Pat. No. 4,106,129 (Carpentier et al.), and U.S. Pat. No. 5,037,434 (Lane), the entire disclosures of which are incorporated herein by reference. These disclosures detail a conventional configuration of three leaflets, with one leaflet disposed between each pair of stent or commissure posts.

Implantation of a stented prosthetic heart valve presents certain technical challenges. For example, a prosthetic mitral valve is normally implanted by placing the prosthesis into the mitral valve annulus with the stent posts projecting blindly deep into the patient's left ventricle. However, due to a lack of visibility through the prosthetic valve, a surgeon can inadvertently loop sutures around the stent posts during suturing of the annular suture ring portion of the prosthesis. Similarly, the extending stent posts may undesirably "snag" on chordae or trabeculae inside the left ventricular cavity. To avoid these complications, various prosthetic valve holders have been designed that inwardly retract or deflect and hold the mitral prosthetic stent posts during implantation. Some of the available prosthetic mitral heart valve holders include an elongated handle and a holder mechanism that is secured to the stent ring and adapted to inwardly deflect the stent posts upon rotation of the handle. An exemplary prosthetic mitral heart valve holder is described in U.S. Pat. No. 4,865,600 (Carpentier et al.). In addition, these concepts can apply to a prosthetic tricuspid valve.

For another example, Medtronic mitral valves are commercially available under the trade designation "Hancock", which valves are mounted to a holder providing a mechanism for inward deflection, as illustrated in the brochures: "A New Dimension—The Hancock II Bioprosthesis", Medtronic Inc., 1991, publication number UC8903226EN and "A New Light on the Hancock Bioprosthesis", Medtronic Inc., 1988, publication number UC8801713EN, both of which are incorporated herein by reference in their entireties. This holder includes a ratcheting spool that is rotatable by means of an attached handle to pull lengths of suture inward, thereby pulling sutures extending upward though the commissure posts and between the commissure posts downward, to thereby deflect the commissure posts inward. In general, these prosthetic mitral heart valve holder devices are well-suited for mitral valve replacement because the mitral valve surgical site is relatively easily accessed, with minimal anatomical obstructions "above" or away from the implant site. Thus, the surgeon is afforded a large, unobstructed area for locating and maneuvering the handle as well as performing necessary procedural steps (e.g., suturing the annulus suture ring to the heart tissue) with minimal or no interference from the handle and/or mechanism.

Aortic and pulmonic prosthetic heart valve implantation, however, presents different constraints from those associated with mitral or tricuspid valve replacement because there is less room for the surgeon to maneuver during the surgery. In particular, depending upon the type of aortotomy performed, the surgeon may first have to pass the prosthesis through the sinotubular junction, which is typically smaller than the tissue annulus onto which the prosthetic heart valve will be sutured. Because the stent posts extend proximally toward the surgeon in aortic and pulmonic valve replacement (as opposed to the distal stent post direction associated with mitral and/or tricuspid valve replacement), the chances of inadvertently looping sutures about stent post(s) is minimal. However, the proximally extending stent posts associated with the stented prosthesis still can interfere with the various other maneuvers required of the surgeon.

In light of the above, it can be desirable to inwardly deflect the stent posts during implantation of the aortic and/or pulmonic prosthetic heart valve. Unfortunately, the above-described mitral and tricuspid prosthetic heart valve holders are of little value for aortic and pulmonic valve replacement procedures in that these holders position the holder and handle to extend in a direction opposite from that of the stent posts. As such, the holder and handle would have to be removed in order to implant the aortic prosthetic heart valve. Certain approaches have been taken to correct this incompatibility by reconfiguring the holder and handle to extend in a direction similar to the stent posts on the outflow side of the valve, as described, for example, in U.S. Pat. Nos. 5,476,510 (Eberhardt et al.) and 5,716,410 (Eberhardt et al.), the entire disclosures of which are incorporated herein by reference.

There is a continued need to provide different devices for assisting in the implantation of stented prosthetic heart valves that can be used in any area of the heart, including devices that can be used for implantation of aortic prosthetic heart valves. In particular, a need exists for a stent post deflection device that is simple and effective to use for areas of the heart that are typically difficult to access by the surgeon, such as for aortic heart valve replacement.

SUMMARY OF THE INVENTION

The present invention is directed to a valve holder attached to a bioprosthesis to assist the surgeon in valve implantation. In particular, the valve holder of the invention can be used for aortic valve replacement, and provides for temporary deflection of stent posts of the prosthesis, such as an aortic prosthetic heart valve. This deflection of the stent posts helps to ease the implantation process, and also increases the space available for the surgeon to manipulate the sutures and tie suture knots. The holder of the invention is attached to the tips of the stent posts, which thereby provides an open space between the commissures and behind the stent posts for easier access to the sutures, such as for knot tying which can also reduce the time required for implantation. Other benefits include, but are not limited to: reduced cardiopulmonary bypass time; reduced potential for injury to patient's aorta during knot tying; the ability to implant a larger valve and resulting hemodynamic benefit; increased visibility to knots and a resultant reduction in potential for paravalvular leakage; and potential for less damage to the prosthetic valve during knot tying due to insufficient access.

The valve holder of the invention includes stent posts that can be deflected prior to or after handle attachment via a pinching motion toward the center or base of the valve holder. In particular, a snap-fit connection serves to lock the holder and stent posts in their deflected positions until the holder is removed by cutting the suture or sutures that attach the stent posts to the holder. The amount of stent post deflection can be predefined to one or more predetermined deflection positions, where each of these positions reflects a certain distance between the stent post tip and the handle of the valve holder. The amount that each stent post is deflected is preferably uniform across all stent posts for a particular implantation procedure, although it is possible that only some of the stent posts are deflected or that the stent posts are deflected by different amounts.

In one embodiment, a valve holder is provided for a prosthetic valve having a stent comprising a stent base and multiple commissure posts projecting from the stent base. The holder comprises a handle that is attachable and detachable from a base member, wherein the base member comprises a plurality of extending legs. Each of the extending legs preferably comprises two prong portions spaced from each other by a gap. The holder further comprises a commissure post engaging member slideably engageable with the distal end of each of the extending legs. These engaging members are attachable to a commissure post of the prosthetic valve, such as with the use of a suture. The relationship between the engaging members and their corresponding extending legs preferably provides at least two positions for the commissure posts; an undeflected position and a compressed or deflected position. The deflected position of the stent posts is a preferable configuration to allow positioning of the prosthetic valve during placement and securing of the prosthetic valve during surgery. The sutures that are holding the commissure posts of the stent to the commissure post engaging members may then be severed and the valve holder can be removed from the patient.

The invention further includes a method of installing a prosthetic valve in a patient, the prosthetic valve having a stent comprising a stent base and multiple commissure posts projecting from the stent base. The method comprises the steps of providing a valve holder comprising a base portion and a handle extending from the base portion, a plurality of legs radially extending from the base portion, and a plurality of commissure post engaging members, each of which is slideably engaged with one of the plurality of legs; attaching each of the commissure post engaging members to one of the multiple commissure posts of the stent with the commissure post engaging members in a first position; sliding each of the commissure post engaging members on its respective leg to a second position, wherein the commissure posts are deflected inwardly as compared to the first position; positioning the valve holder with the attached prosthetic valve at an implantation site of a patient; and suturing the prosthetic valve to tissue of the patient. The prosthetic valve may be an aortic prosthetic heart valve. The method may include attaching each of the commissure post engaging members to one of the multiple commissure posts of the stent by a suturing step. The method may also include the steps of detaching the valve from the valve holder and removing the valve holder from the patient.

BRIEF DESCRIPTION OF THE DRAWINGS

The invention will be further explained with reference to the appended Figures, wherein like structure is referred to by like numerals throughout the several views, and wherein:

FIG. 4 is a perspective view of the base member of the valve holder of FIG. 3a;

FIG. 5 is a top view of the base member of FIG. 4;

FIG. 6 is a side view of the base member of FIG. 4;

FIG. 9 is a perspective front view of one commissure post engaging member of the type illustrated in FIG. 3a;

DETAILED DESCRIPTION

Figure 1:
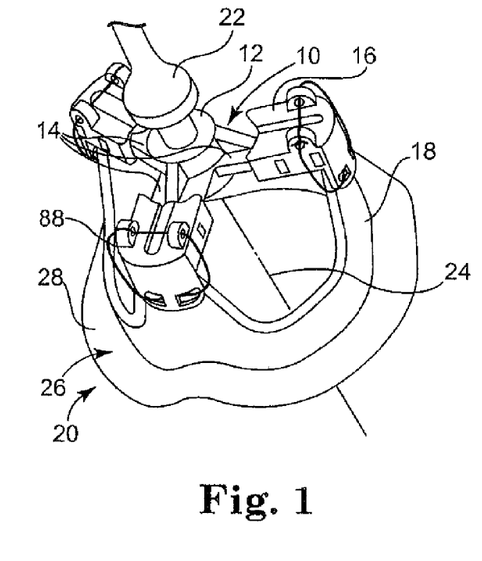
FIG. 1 is a perspective view of one embodiment of a portion of a valve holder of the invention, where the valve holder is attached to the top of the stent posts of a prosthetic heart valve, which posts are shown in their undeflected condition, and which also illustrates a handle.
Figure 2:
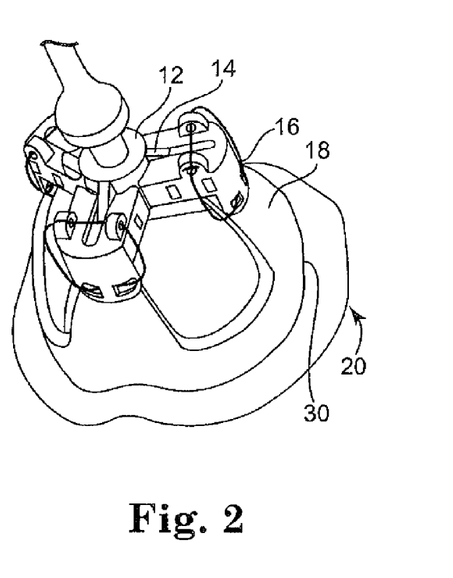
FIG. 2 is a perspective view of the valve holder of FIG. 1, with the valve holder shown as deflecting the posts of the prosthetic heart valve toward the center of the valve holder.

Referring now to the Figures, wherein the components are labeled with like numerals throughout the several Figures, and initially to FIGS. 1 and 2, a perspective view of one embodiment of a portion of a valve holder 10 of the invention is illustrated. The valve holder 10 generally includes a base member 12 that includes three extending legs 14, and a commissure post engaging member 16 slideably received onto the distal end of each of the extending legs 14. As shown, each of the engaging members 16 is attached to the top of one of three stent posts 18 of a prosthetic heart valve 20, which stent posts 18 are shown in their undeflected condition in FIG. 1 and in their deflected condition in FIG. 2. In general, the engaging members 16 are positioned closer to the center of the base member 12 when the stent posts 18 are deflected (e.g., FIG. 2) than when the stent posts 18 are not deflected (e.g., FIG. 1).

Valve holder 10 further includes a handle 22 that is attachable to and detachable from the base member 12 at a distal end of the handle 22. In one preferred embodiment, the connection between the handle 22 and base member 12 is accomplished via a threaded connection, where the end of the handle 22 has outer threads that are compatible for connection with inner threads of a generally central opening in base member 12. However, the handle 22 may be connectable to the base member 12 in a number of different ways that allow the surgeon to attach and detach these two components with relatively minimal effort, when desired. The handle 22 can be made of stainless steel or another suitably rigid, sterilizable material. Handle 22 defines a central, longitudinal axis 24 of valve holder 10. Exemplary handle connections can incorporate a pivot joint to enable optimum positioning of the handle and/or use a shape memory material (e.g., nitinol). Another exemplary embodiment of the handle may additionally include a reduced diameter portion along its length for enabling the handle to be bent to a desired angle during the valve implant procedure. Commercially available handles that may be used include those available from Medtronic Inc. of Minneapolis, Minn. under the trade designation "Mosiac" and "Hancock II."

As referred to herein, the prosthetic heart valves 20 used with the invention may include a wide variety of different configurations, such as a prosthetic heart valve having tissue leaflets or a synthetic heart valve having polymeric leaflets, and can be specifically configured for replacing any heart valve. That is, while much of the description herein refers to replacement of aortic valves, the valve holder of the invention can also generally be used for replacement of pulmonic valves, for use as a venous valve, or to replace a failed bioprosthesis, such as in the area of an aortic valve or mitral valve, for example. In any case, exemplary prosthetic heart valves 20 used with the present invention generally include a stent 26 including a sewing ring 28 from which three stent posts 18 extend. All or a portion of the stent 26, including the sewing ring 28 and stent posts 18, is preferably covered by a flexible covering 30, which may be a fabric, polymer, cloth, or tissue material to which leaflets (not shown) of the valve 20 can be sewn. Further, as is known in the art, the internal structure of each of the stent posts 18 is formed of a stiff but resiliently bendable material. This construction allows the stent posts 18 to be deflected from the orientation shown in FIG. 1 to the orientation shown in FIG. 2 by the application of an external force. Once this external force is removed or reduced, the stent posts 18 will then move at least partially back toward the orientation shown in FIG. 1.

Figure 3A:
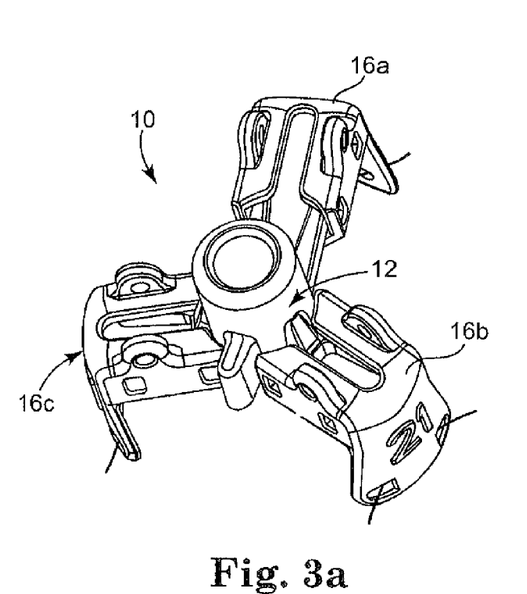
FIG. 3a is another perspective view of an embodiment of a valve holder of the invention, showing two commissure post engaging members in their compressed condition and one commissure post engaging member in its undeflected condition.

Referring now to FIG. 3a, another perspective view of valve holder 10 is shown without a corresponding heart valve 20. In this Figure, one of the commissure post engaging members 16a is shown in the position it will be in when its corresponding stent post is not deflected, and the other two commissure post engaging members 16b, 16c are shown in the position they will be in when they are radially deflecting their corresponding stent posts inward toward the longitudinal axis 24 of valve holder 10.

Figure 3B:
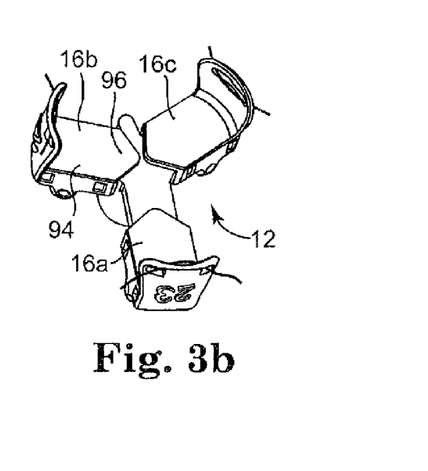
FIG. 3b is a bottom perspective view of the valve holder of FIG. 3b.

FIG. 3b illustrates one configuration of the bottom of the valve holder 10, with two of the commissure post engaging members 16b and 16c in their deflected positions and one member 16a in its undeflected position. As shown, a bottom surface 94 of each of the engaging members 16a, 16c includes an angled tip portion 96, which provides additional stability to the valve holder 10 when the members are in their undeflected condition, while allowing for maximum use of the free space in the center of base portion 12 when the engaging members 16a-16c are all pushed toward the center of the holder 10 (i.e., when in their deflected positions). The extra stability can be particularly advantageous when pressing down on the handle when the engaging members are in their undeflected position.

The bottom surfaces 94 of each of the post engaging members may have an identical size and shape to the bottom surfaces 94 of the other post engaging members of a particular valve holder, which would allow for ease in manufacturability and assembly of the valve holder. If the extending legs on which the post engaging members are mounted are not evenly spaced from each other, however, the surfaces of the angled tip portions 96 will also be spaced differently from each other around the central portion. Thus, the shape and size of the bottom surfaces 94 and their respective tip portions 96 can be designed and selected to achieve a desired spacing of the components when in both their compressed and uncompressed positions. In that regard, it is also contemplated that the bottom surfaces 94 of each post engaging member of a single valve holder can be differently sized, shaped and/or configured than the bottom surfaces of the other post engaging members. In a further alternative, one or more of the post engaging members can be provided without any angled tip portion and may instead include a different tip or end shape, such as flat, curved, or other alternative shapes.

FIGS. 4-8 provide multiple views of one exemplary embodiment of the base member 12 of the invention, which includes three extending legs 14 projecting from a central portion 36. Each of the extending legs 14 includes two prongs 32 spaced from each other by a distance that varies across a gap 34. Prongs 32 each include an enlarged portion or tab 38 at their distal ends (i.e., the ends that are spaced furthest from the central portion 36). These portions 38 are designed to engage with corresponding portions of commissure post engaging members 16, and gap 34 is configured to accept a corresponding portion of commissure post engaging members 16, both of which will be described in further detail below. In any case, each prong 32 is preferably strong enough to support the structure of a commissure post engaging member 16 that will be mounted thereon, yet is preferably flexible enough to be able to be moved at least slightly when compressed toward the other prong 32 of its extending leg 14.

The extending legs 14 may alternatively be configured differently than the two prongs spaced from each other with a gap between them, as described above. For example, the legs may include a unitary piece that is compressible or flexible in the areas of portions that are designed to engage with corresponding portions of commissure post engaging members. For another example, the commissure post engaging members 16 may have compressible or flexible portions in their internal area that are designed to engage with rigid acceptor openings on the extending legs. For yet another example, the legs may include a multi-tooth slide or ratchet mechanism that engages with apertures or engaging surfaces of the commissure post engaging members to provide multiple deflection amounts and positions.

Figures 4, 5, 6:
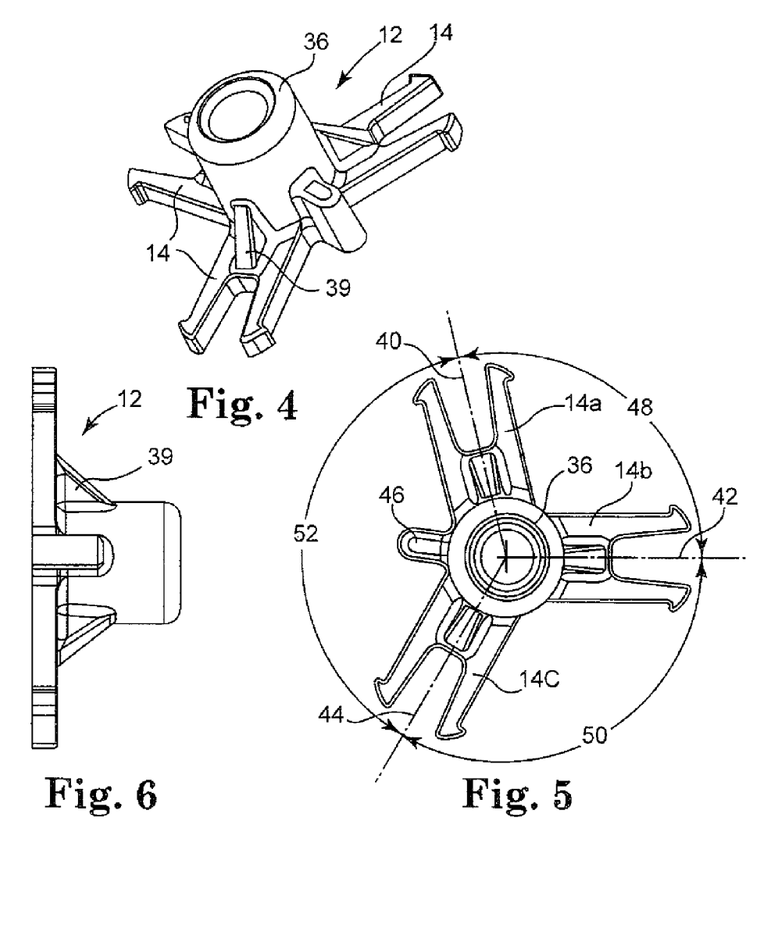
Figure 7:
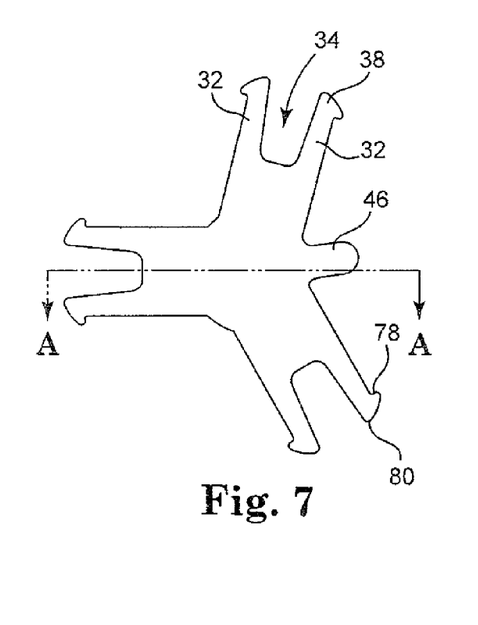
FIG. 7 is a bottom view of the base member of FIG. 4.
Figure 8:
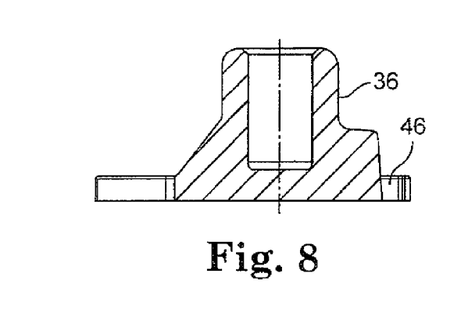
FIG. 8 is a cross-sectional side view of the base member of FIG. 7, taken along section line A-A.
Figure 9:
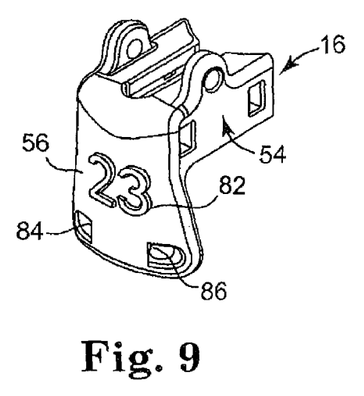
Figure 10:
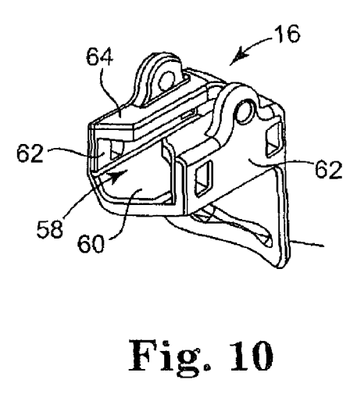
FIG. 10 is a perspective back view of the commissure post engaging member of FIG. 9.
Figure 11:
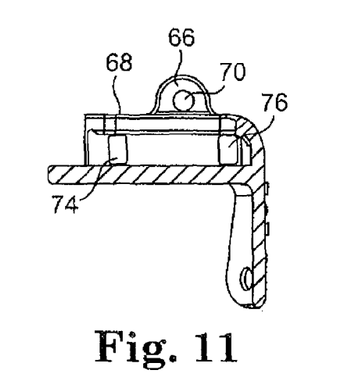
FIG. 11 is a cross-sectional side view of the commissure post engaging member of FIG. 9.
Figure 12:
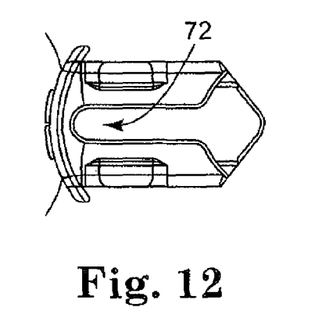
FIG. 12 is a top view of the commissure post engaging member of FIG. 9.
Figure 13:
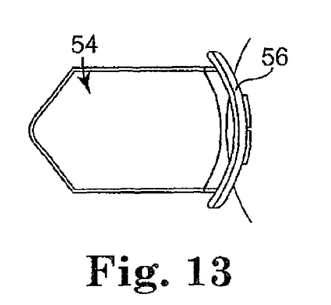
FIG. 13 is a bottom view of the commissure post engaging member of FIG. 9.

One exemplary spacing of the extending legs 14a, 14b, 14c from each other around the periphery of central portion 36 is illustrated in FIG. 5. In particular, extending leg 14a is positioned so that its central axis 40 is at an angle 48 of 105 degrees from a central axis 42 of extending leg 14b, and central axis 42 of extending leg 14b is positioned at an angle 50 of 120 degrees from a central axis 44 of extending leg 14c. It follows that central axis 44 of extending leg 14c is spaced at an angle 52 of 135 degrees from central axis 40 of extending leg 14a. These angular locations and spacings of the extending legs 14a, 14b, 14c from each other can be selected to correspond with the spacing of the leaflets from each other in an aortic valve, for example, which therefore results in the unequal spacing described above. However, it is understood that the spacing of the extending legs 14a, 14b, 14c from each other can vary widely from the relationships illustrated in FIG. 5, and the angles between adjacent legs may be identical around the circumference of central portion 36. Further, if a valve holder includes more or less than three legs (i.e., as may be used with a prosthetic valve having more or less than three leaflets), the spacing of the legs from each other can be chosen to accommodate a patient's anatomy, certain valve characteristics, and the like.

Base member 12 further can include an optional indicator portion 46, which may be particularly useful in cases where the extending legs 14a, 14b, 14c are not equally spaced from each other around central portion 36. This indicator portion 46 can be used by the surgeon and/or other operating room personnel as an aid to properly orienting the valve holder 10 relative to a valve and/or other components or anatomical features. In the exemplary embodiment of FIG. 5, the indicator portion 46 is positioned generally in the center of the space between adjacent legs 14a, 14c, thereby providing a visual and tactile indicator that the spacing between adjacent legs in this area is 135 degrees. In addition, it is contemplated that markings can be placed on the holder to indicate the largest stent opening and/or various degrees of deflection, cut points, valve size, handle insertion or deflection release points.

Referring now to FIGS. 9-13, multiple views of one embodiment of a commissure post engaging member 16 of the invention are illustrated. Engaging member 16 includes a first or horizontal portion 54 and a second or vertical portion 56 that extends generally perpendicular to first portion 54, although it is contemplated that the first and second portions 54, 56 are angled relative to each other in a non-perpendicular relationship. First portion 54 includes a channel 58 that is sized to slideably engage with a corresponding extending leg 14 of a base member 12. Channel 58 comprises a bottom surface 60, two side surfaces 62 spaced from each other on opposite sides of channel 58, and a top surface 64 spaced from bottom surface 60. Side surfaces 62 each include a suture loop 66 extending from their top edge 68, although the suture loops 66 may be wide enough, as shown, that they can be considered to additionally or alternatively extend from the top surface 64. In any case, suture loops 66 include an aperture 70 for receiving a suture that can extend between suture loops 66 on opposite sides of the engaging member 16. Top surface 64 further may optionally further include a notch 72 between the suture loops 66, which can provide easier access for the surgeon to cut the suture, as will be explained in further detail relative to the methods of surgically using the valve holders of the invention.

Side surfaces 62 each include at least two apertures 74, 76 that are spaced from each other along the length of the channel 58. Apertures 74, 76 are arranged and sized to engage with tabs or enlarged portions 38 of extending legs 14, and are preferably provided in matching pairs across the width of channel 58. It is possible, however, that the number and positioning of such apertures can be different from each other on the two side surfaces 62. Side surfaces 62 are spaced from each other across the width of channel 58 so that when a corresponding extending leg 14 is inserted therein, the prongs 32 are initially compressed at least slightly toward each other. The extending leg 14 is then pushed further into the channel 58 until the tabs or enlarged portions 38 of prongs 32 are aligned with the first set of apertures 74 on side surfaces 62. Tabs 38 can then move into the apertures 74, thereby allowing the prongs 32 to move at least slightly away from each other and providing a temporary locking position for the extending leg 14 relative to the engaging member 16. This position represents an expanded or uncompressed condition of the valve holder.

In order to advance each extending leg 14 toward the compressed condition of the valve holder, the extending leg 14 can be pushed even further into the channel 58 and toward the second set of apertures 76. However, in order for this to occur, the tabs 38 must first be disengaged from the apertures 74. Depending on the configuration of the tabs 38, this may be accomplished either by simply pressing on the engaging member 16 until the tabs 38 are moved out of engagement with the apertures 74, or some type of tool or instrument can be used to press the prongs 32 toward each other until the tabs 38 are not engaged in the apertures 74, then pressing the engaging member 16 toward the central portion 36 of base member 12 until the tabs 38 are aligned with the second set of apertures 76 on side surfaces 62. Tabs 38 can then move into the apertures 76, thereby allowing the prongs 32 to move at least slightly away from each other, and providing a locking position for the extending leg 14 relative to the engaging member 16. This position represents the compressed or deflected condition of the valve holder 10, which is illustrated with a valve holder in FIG. 15.

In order to allow movement of the extending legs 14 into the channels 58 in the manner described above, the tabs 38 of this exemplary embodiment are tapered at their distal ends 80 to allow smooth movement of the prongs 32 into the channel 58, as shown, for example, in the embodiment of FIGS. 4-7. However, the tabs 38 can further be configured as shown with a blunt edge 78 on the side opposite the distal ends 80 so that "backward" movement of the extending legs 14 relative to the engaging members 16 (i.e., away from longitudinal axis 24 of valve holder 10) cannot be accomplished by simply pulling the components in opposite directions relative to each other, but instead requires the use of a tool or other device to compress the tabs 38 and their corresponding prongs 32 toward each other to release the components so that they are slideable relative to each other.

As described above, the relationship between the extending legs 14 and the engaging members 16 provides for two "set" or secure positions for these components relative to each other (i.e., when the tabs 38 are secured within the apertures 74 or 76). In these positions, the user may be able to determine the positions of the components simply by tactile or visible observance of the devices snapping in place relative to each other. However, it is possible that additional apertures may be provided along the side surfaces 62 and/or that the prongs 32 of extending legs 14 may have additional tabs for engagement with different apertures. It is further contemplated that the tabs 38 can have a different configuration, such as having a more sloped or rounded surface, being more rectangular, or even facing in an opposite direction so that a tapered portion of the tabs is spaced from the distal end of the extending arms.

Referring again to FIGS. 4-8, base member 12 may further includes optional support members 39 that extend at an angle from central portion 36 to the top surface of each of the extending legs 14. Support members 39 provide stability to the legs 14 to minimize deflection thereof and also are configured to fit into gap or notch 72 in the top surface of engaging member 16 when the engaging members are in their deflected or compressed position. In this way, relative motion between the legs 14 and engaging members 16 can be minimized.

Referring again to FIG. 9, vertical portion 56 of commissure post engaging member 16 further comprises at least a first suture aperture 84 and preferably also includes a second suture aperture 86 spaced across the width of vertical portion 56. The use of these apertures 84, 86 can best be explained by additionally referring to FIGS. 1 and 2. In particular, a suture 88 is illustrated, which extends through apertures 70 of the two suture loops 66 and also through first suture aperture 84 and second suture aperture 86. In the area between first and second suture apertures 86 and on the interior side of vertical portion 56, the suture is sewn onto stent post 18, thereby securing the engaging member 16 to the stent post 18. As shown, each of the stent posts 18 and engaging members 16 have an individual suture that secures them to each other, although it is possible that a single piece of suture material can be used for securing all three of the stent posts 18 to engaging members 16. It is further understood that the engaging member 16 may be provided with a different arrangement of apertures to allow for a different suturing pattern for securing each engaging member 16 to each stent post 18. Prior to and during the valve implantation procedure, the valve 20 is maintained relative to valve holder 10 by way of the suture material, which is removed once the sewing ring 28 has been sutured to surrounding tissue in accordance with conventional surgical practice. In addition, the vertical portion 56 preferably has a curvature (see FIG. 13) that is selected to provide more strength to the structure to minimize the thickness of this component. In addition, the curvature of portion 56 is also preferably selected so that the suture apertures 84, 86 are aligned for easier suturing techniques. That is, apertures 84, 86 are preferably arranged so that a single needle can pass through both apertures 84, 86 simultaneously during the suturing process.

Engaging members 16 may optionally include indicia 82 on the outer face of second or vertical portion 56. The indicia 82 may provide information about the sizing of the device, for example, and may be provided on the surface in a number of known ways, such as by engraving, etching, molding or otherwise modifying the surface of the vertical portion 56. Alternatively, the indicia 82 may be adhered, welded, or otherwise attached to the outer surface of the vertical portion 56.

Figures 14, 15, 16:
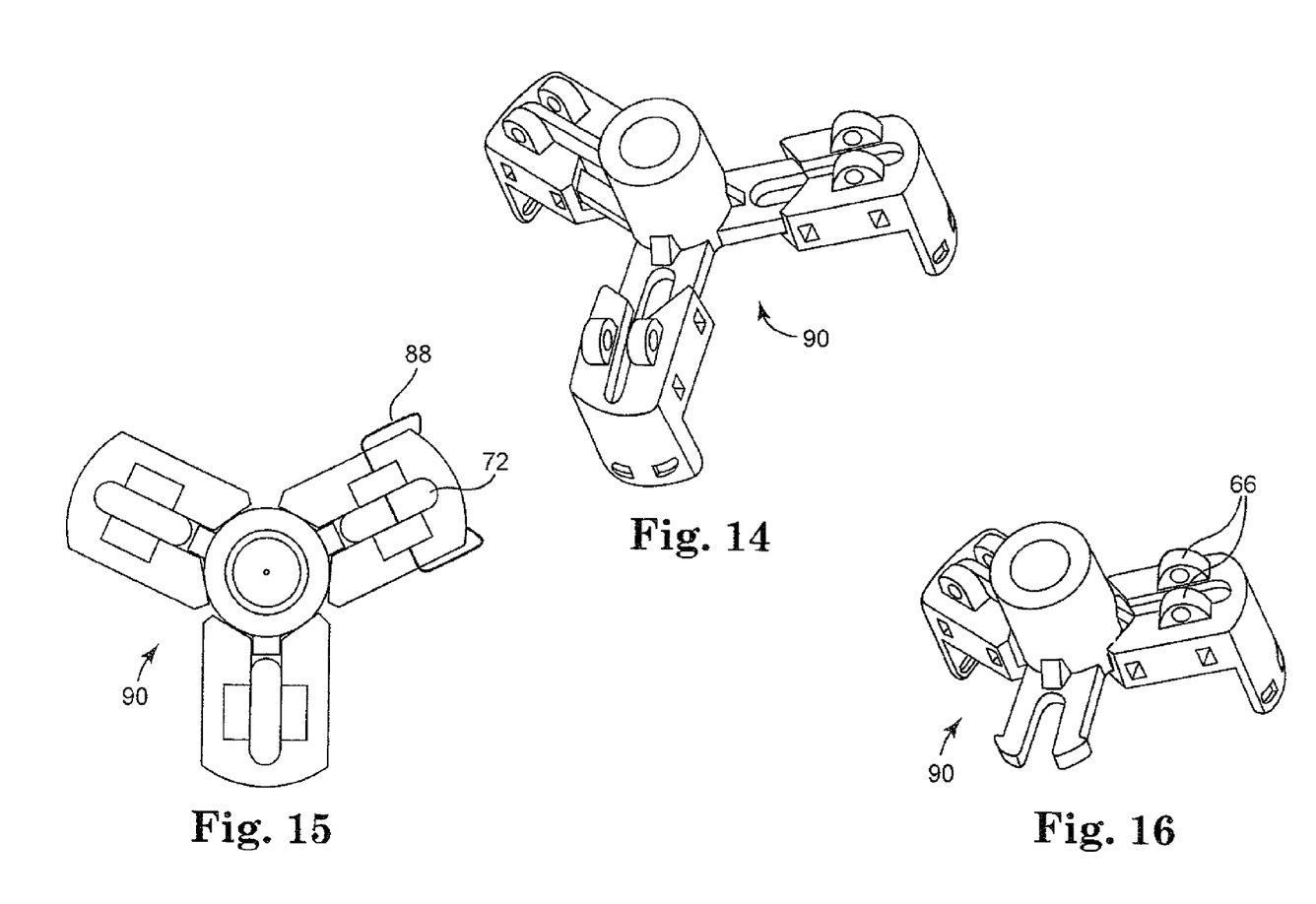
FIG. 14 is a perspective view of a portion of another embodiment of a valve holder of the invention, with the commissure post engaging members in their expanded condition.
FIG. 15 is a top view of the portion of the valve holder of FIG. 14, with the commissure post engaging members in their deflected or compressed condition.
FIG. 16 is a perspective view of a portion of a valve holder of the invention, with a commissure post engaging member mounted on two of the three extending legs.

FIGS. 14-16 further illustrate the features and configurations discussed above, where FIG. 14 illustrates a valve holder 90 in its undeflected condition, FIG. 15 illustrates the same valve holder 90, including a suture 88 threaded through each of the apertures of its commissure post engaging members and showing the valve holder 90 in its deflected condition. FIG. 16 illustrates the same valve holder 90 as is shown in FIG. 15, but with one of the commissure post engaging members removed for a better view of one of the extending legs.

In accordance with the invention and referring again to FIGS. 1 and 2, the sutures 88 may be cut after the device is implanted in the patient, thereby releasing the commissure post engaging members 16 from the stent posts 18 and allowing the valve holder to be removed from the patient. This may be accomplished via the surgeon positioning a small cutting tool in the area between the suture loops 66 on the top of the engaging members 16 and cutting each of the sutures, then removing the suture material from the patient. The notch 72 (see FIG. 12) can assist the surgeon in tactile and/or visual location of the proper areas for cutting the suture. Additionally or alternatively, a component can be provided on the top of the valve holder 10 in the area of the handle 22 that can simply be slid down the shaft of the handle to cut all of the sutures sequentially or simultaneously. For example, a tool that includes a cutting blade for each suture could be provided to cut all three sutures at the same time.

The present invention has now been described with reference to several embodiments thereof. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein.

What is claimed is:

1. A method of installing a prosthetic valve in a patient, the prosthetic valve having a stent comprising a stent base and multiple commissure posts projecting from the stent base, the method comprising the steps of:

providing a valve holder comprising a base portion and a handle extending from the base portion, a plurality of legs radially extending from the base portion, and a plurality of commissure post engaging members, each of which is slideably engaged with one of the plurality of legs, wherein at least one of the legs comprises (i) a first prong portion spaced apart from a second prong portion by a gap distance, and (ii) at least one of the plurality of commissure post engaging members slideably moveable along the leg between fixed positions, the fixed positions being defined by spaced apertures on the at least one of the plurality of commisure post engaging members that cooperate with a tab portion of at least one of the first and second prong portions, wherein the at least one plurality of commissure post engaging members moves the first and second prong portions relative to each other during sliding movement along the leg;

attaching each of the commissure post engaging members to one of the multiple commissure posts of the stent with the commissure post engaging members in a first position;

sliding each of the commissure post engaging members on its respective leg to a second position, wherein the commissure posts are deflected inwardly as compared to the first position;

positioning the valve holder with the attached prosthetic valve at an implantation site of a patient; and suturing the prosthetic valve to tissue of the patient.

2. The method of claim 1, wherein the prosthetic valve comprises an aortic prosthetic heart valve.

3. The method of claim 1, wherein the step of attaching each of the commissure post engaging members to one of the multiple commissure posts of the stent comprises suturing each of the commissure post engaging members to one of the multiple commissure posts of the stent.

4. The method of claim 1, further comprising the steps of:

detaching the prosthetic valve from the valve holder after the prosthetic valve is sutured to the tissue of the patient; and then removing the valve holder from the patient.

* * * * *